United States Patent [19]
Kok

[11] Patent Number: 5,914,273
[45] Date of Patent: Jun. 22, 1999

[54] ANALYTICAL APPARATUS AND METHOD FOR AUTOMATED BLOT ASSAY

[75] Inventor: Lim Jiu Kok, Singapore, Singapore

[73] Assignee: Genelabs Diagnostics Pte Ltd, Singapore

[21] Appl. No.: 08/486,432

[22] Filed: Jun. 7, 1995

Related U.S. Application Data

[62] Division of application No. 08/401,662, Mar. 9, 1995, Pat. No. 5,567,595, which is a continuation of application No. 08/284,281, Aug. 2, 1994, abandoned, which is a continuation of application No. 07/926,018, Aug. 7, 1992, abandoned, which is a continuation of application No. 07/448,114, Dec. 13, 1989, abandoned.

[51] Int. Cl.$^6$ .................................................. G01N 33/543
[52] U.S. Cl. .......................... 436/518; 422/101; 422/102; 435/286.7; 435/286.2; 435/288.3; 435/288.5
[58] Field of Search ........................... 422/58, 68.1, 100, 422/102, 101, 104; 435/7.92, 291, 300, 301, 312, 809, 286.7, 287.2, 288.3–5; 436/180, 809, 518

[56] References Cited

U.S. PATENT DOCUMENTS

| | | |
|---|---|---|
| 3,226,094 | 12/1965 | Margolis . |
| 3,535,208 | 10/1970 | Sasaki et al. . |
| 4,031,197 | 6/1977 | Marinkovich . |
| 4,076,592 | 2/1978 | Bradley ........................... 195/103.5 K |
| 4,128,628 | 12/1978 | Brooker et al. . |
| 4,181,501 | 1/1980 | Keese et al. . |
| 4,244,694 | 1/1981 | Farina et al. . |
| 4,314,968 | 2/1982 | Guigan . |
| 4,330,080 | 5/1982 | Mathieu .................................... 233/27 |
| 4,378,438 | 3/1983 | Masaki et al. ........................... 435/301 |
| 4,383,041 | 5/1983 | Kutsusawa et al. . |
| 4,412,973 | 11/1983 | Guigan ..................................... 422/72 |
| 4,431,606 | 2/1984 | Revillet et al. ......................... 422/102 |
| 4,448,890 | 5/1984 | Smetana et al. . |
| 4,452,901 | 6/1984 | Gordon et al. . |
| 4,470,954 | 9/1984 | Chiknas .................................... 422/72 |
| 4,520,113 | 5/1985 | Gallo et al. . |
| 4,626,684 | 12/1986 | Landa . |
| 4,681,742 | 7/1987 | Johnson et al. . |
| 4,690,801 | 9/1987 | Anderson . |
| 4,716,109 | 12/1987 | Baker et al. . |
| 4,720,463 | 1/1988 | Farber et al. . |
| 4,725,406 | 2/1988 | Compton et al. . |
| 4,764,342 | 8/1988 | Kellin et al. .............................. 422/72 |
| 4,859,419 | 8/1989 | Marks et al. . |
| 4,997,768 | 3/1991 | Uffenheimer et al. ..................... 436/45 |
| 5,053,197 | 10/1991 | Bowen ...................................... 422/58 |
| 5,147,607 | 9/1992 | Mochida ................................... 422/57 |
| 5,580,790 | 12/1996 | Wahl et al. ............................... 436/45 |
| 5,744,096 | 4/1998 | Jones et al. ............................... 422/58 |

FOREIGN PATENT DOCUMENTS

| | | |
|---|---|---|
| 0030086 A1 | 5/1981 | European Pat. Off. . |
| 2193315 | 2/1988 | United Kingdom . |
| WO/85/04903 | 11/1985 | WIPO . |
| WO86/02168 | 4/1986 | WIPO . |
| WO/89/09389 | 10/1989 | WIPO . |

*Primary Examiner*—James C. Housel
*Assistant Examiner*—Ginny Allen Portner
*Attorney, Agent, or Firm*—Allan A. Brookes; LeeAnn Gorthey

[57] ABSTRACT

The invention is an apparatus and method for performing the Western Blot Assay and other assays. The invention includes a tray within which multiple samples can be assayed with a minimum of operator attention. The tray that is desirably used with the apparatus is multichambered and can be alternately agitated and drained according to drive cards and/or other controls such as electronic controls. The tray is designed in such a way that reagents and washing fluids, which are added sequentially and then cleared, do not back flow into the chambers of the tray.

7 Claims, 6 Drawing Sheets

ANALYTICAL APPARATUS AND METHOD FOR AUTOMATED BLOT ASSAY

This application is a division of application Ser. No. 08/401,662 filed Mar. 9, 1995, now U.S. Pat. No. 5,567,595, which is a continuation of application Ser. No. 08/284,281, filed Aug. 2, 1994, now abandoned, which is a continuation of application Ser. No. 07/926,018, filed Aug. 7, 1992, now abandoned, which is a continuation of application Ser. No. 07/448,114, filed Dec. 13, 1989, now abandoned, all of which are hereby incorporated by reference.

BACKGROUND OF THE INVENTION

1. Field of the Invention

The present invention is related to automated and semi-automated immuno-assays and methods for performing an immuno-assay. Specifically, this invention is an automated apparatus and method for performing blot assays such as the Western Blot Assay.

2. Description of the Background Art

Currently available automated and semi-automated assays are based primarily on an enzyme-linked immunosorbent assay (ELISA). An ELISA is used to detect proteins including antigens and antibodies. Once a positive result is obtained with an ELISA, a Western Blot Assay is often used to more accurately analyze or confirm the analysis. The Western Blot Assay provides a sensitive analysis, but is not currently performed by an automated means. For this reason, the performance of a Western Blot Assay for similar assay requires many manual procedures and is, therefore, expensive and subject to human error. The operator of such an analysis is at some risk of contact with the pathogens that are being analyzed.

U.S. Pat. No. 4,520,113 to Gallo et al. discloses a method for detecting antibodies characteristic of AIDS using antigen from the virus HTLV-III. Antigens associated with this virus are specifically recognized by antibodies from AIDS patients. The detection of the antigen is performed by strip radioimmunoassay based on the Western Blot technique, ELISA (most preferred), or indirect immunofluorescence assay. This method is not automated.

PCT Application No. 8,504,903 by Gallo et al. discloses use of a Western blot and a competition immunoassay to detect HIV antibodies. Protein bands are formed by electrophoresis of HIV on a polyacrylamide gel in the presence of sodium dodecyl sulphate. The bands are transferred to a nitrocellulose sheet which is then separated into strips. The strips are then used as antigenic reagents in a competition immunoassay. The test can be used in screening for AIDS. The test is not automated, and does not provide safety or convenience.

Gordon, U.S. Pat. No. 4,452,901 describes the electrophoretic transfer of proteins from gels to nitrocellulose. The immobilized proteins may then be used for the immunodetection of antigens or antibodies.

U.S. Pat. No. 4,720,463 to Farber et al. discloses an automated microbiological testing apparatus. An incubation chamber holds multiple microbiological test trays. Tray carriers move the trays to an inspection station. The image on the tray is processed to determine test results. This apparatus and method allows neither rocking of the samples nor the automatic sequential addition and removal of reagents and washing solutions.

U.S. Pat. No. 3,535,208 to Sasaki et al. discloses an apparatus that provides a rocking motion for samples. The primary purpose of the rocking motion in this invention is to provide heat transfer. Each sample in a series of samples has a different proportion of its wall or container surface area in contact with a heating or cooling chamber. Each sample, therefore, reaches a different temperature during the rocking motion. This apparatus allows temperature dependence of a reaction to be determined in a single apparatus with a single experiment. The apparatus does not allow the sequential addition and removal of reagents and washing solutions.

The industry is lacking a fully automated means for performing the Western Blot Assay and similar assays that is economical, safe, accurate, and convenient to use.

SUMMARY OF THE INVENTION

One object of the invention is to overcome the deficiencies of the prior art by automating the sequential addition and removal of reagents and washing solutions, and the agitation of the reaction mixtures to produce the desired reactions.

The apparatus of this invention comprises a tray as a reaction vessel, dispensing means for introducing at least one solution into the tray, means for rocking the tray to assure a uniform mixture of the reaction components, means for draining the tray to remove solutions when appropriate, and control means for controlling the dispensing, rocking and draining means. The control means is designed or programmed to coordinate the dispensing of solutions into the tray, and the rocking and draining of the tray, according to a predetermined schedule and in a highly reproducible manner.

In a preferred embodiment, one of the reaction components is an insoluble reaction means ("strip means") which is placed in the tray in the beginning of the procedure. The tray preferably retains a plurality of these strip means in separate channels.

The tray is adapted to retain the solution during rocking, but allow it to escape during a drainage step. It preferably also includes structure for retaining the strip means in place during the drainage step.

The present method improves productivity in analytical laboratory since it reduces the amount of handling required. Moreover, by eliminating manual addition of reagents and wash solution, the opportunities for human error are reduced. Safety is also promoted, since the technician is less likely to come into direct contact with the samples.

DESCRIPTION OF THE PREFERRED EMBODIMENTS

The invention is an automatic apparatus that can be used to perform assays (especially blot immunoassays) safely, accurately, and conveniently. The automatic apparatus comprises a sample tray with a means for dispensing reagents and washing solutions to the sample tray, a means for rocking and draining the sample tray, and a means for controlling the timing and sequence of the dispensing, rocking, and draining functions of the apparatus.

The apparatus may be used in an assay for, e.g., AIDS virus-specific antibodies in sera. In such an assay the strip means bear an AIDS virus antigen. A patient's serum is incubated with the strip means. The apparatus of this invention then dispenses a series of reagents and washing solutions onto the strip means that is positioned in a tray. The apparatus rocks the tray in order for the dispensed solutions to be evenly dispersed over the reaction strip. The tray containing the strip means in this embodiment is in a closed compartment and is incubated. The tray is canted and held at an angle that permits the solution or solutions to drain from the tray. The apparatus can be programmed in desirable embodiments to perform a variety of rocking and draining cycles with each cycle having a preselected period of time within which to occur. The control logic can be modified to accommodate other assays or other procedures.

After start-up activities such as pump priming and sample introduction, the apparatus automatically performs a sequence of dispensing, agitating, draining, and washing steps. An alarm can be provided to notify the operator that the test is completed. Thus, constant attendance is not required.

Figure 1:
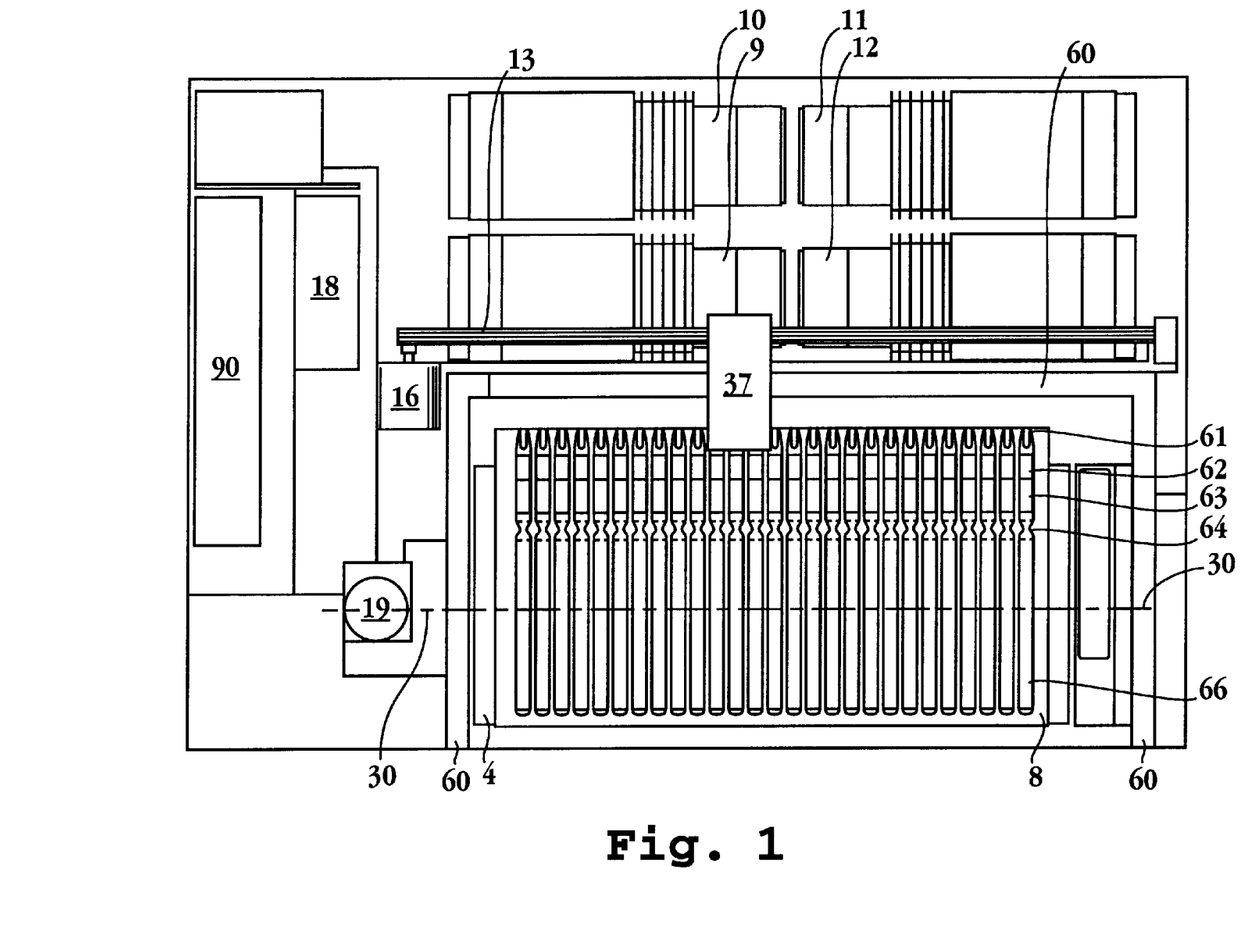
FIG. 1 is a top plan view of the Automated Western Blot Assay apparatus.

FIG. 1 discloses the preferred embodiment of the layout of major components of the apparatus. A sample tray 8 is affixed to a sample tray support 4 in an incubation chamber 60. The sample tray 8 is rocked and drained by a step motor 19 about an axis of rotation 30. Solutions held in the area 90 are pumped by the pumps 9, 10, 11, and 12 through a dispenser 37 controlled by a step motor 16 which moves the dispenser along a track 13. A programmable logic circuit 18, as well as other circuitry and motor drive cards, control the various functions of the apparatus.

The following approximate physical specifications are used with desirable embodiments of the apparatus. The length is 60 to 100 cm, desirably 70 cm. The width 40 to 80 cm, desirably 52.5 cm. The height is 45 to 90 cm, desirably 59 cm. The weight 10 to 25 kg, desirably 14 kg. These dimensions provide a commercially desirable apparatus that can be readily used in most laboratories for performing immuno-assays.

The following operating specifications are used with desirable embodiments of the apparatus and method of this invention. Input voltage for the apparatus can be 110 or 220 volts. Operating temperature range from room temperature to about 200 degrees Celsius. A default setting of 37 degrees Celsius and an overheat temperature setting of 45 degrees Celsius are desirable.

The sample tray 8 comprises at least one and usually a plurality of multi-sectioned, elongated compartments, each compartment having the same configuration. Each strip section holds a "strip means", an article comprising a reactant immobilized on a support. In an immunoassay, the reactant will usually be an antigen or antibody. In other assays, the insolubilized reactant may be, e.g., a chromogen. The immobilized reactant may be a component of a sample, or it may be a reagent which acts upon the sample or upon another reagent (e.g., a secondary antibody which binds a primary antibody). The support may be fabricated out of any material suitable for immobilizing the reaction component, e.g., polyethylene, nitrocellulose, nylon, glass, etc. The support may also be of any desired size or form which can be accommodated by the strip section of the tray; strips are, however, preferred.

The reaction component may be reversibly or irreversibly immobilized on the support by any art-recognized technique. It may be bound covalently, or noncovalently, and directly or indirectly.

In the "Western blot" technique, proteins are transferred from gels to a solid support such as nitrocellulose. The protein becomes bound to the nitrocellulose as a result of noncovalent (e.g., hydrophobic) interactions. The nitrocellulose bearing the proteins may be cut into strips and used as the strip means of the present invention. In a Western Blot Assay, a support bearing proteins transferred to it by the "Western blot" technique are used as solid phase reagents in an immunoassay for antibodies against such proteins.

The strip means is sequentially exposed to other reaction components, such as samples, reagents, and washing solutions. At the end of the assay sequence, the assay results are determined.

The samples of the present invention may be biological fluids such as sera, urine, milk and the like, or tissues which have been solubilized for assay purposes. The reagents may be antibodies (or other binding proteins), antigens (or other target molecules), enzymes, enzyme substrates, chromogens, and the like.

Desirably, the strip section is about 10 cm long and 1 to 2 cm wide and slightly larger than the strips. Desirably, there are 27 compartments in a sample tray, including 25 compartments for samples and one each for a positive and a negative control.

Figure 2:
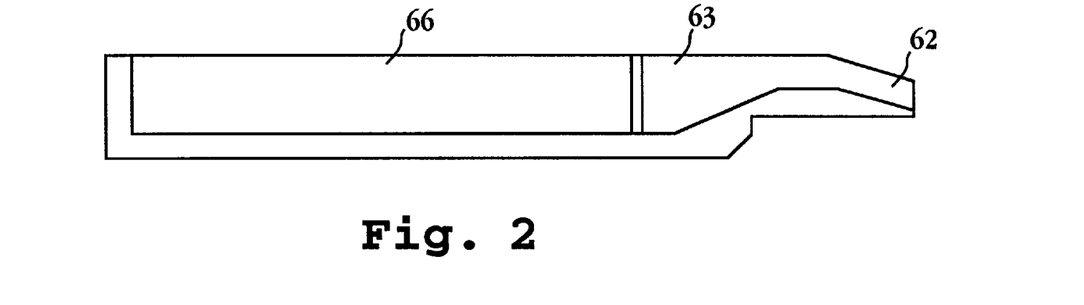
FIG. 2 is a side view of a sample compartment in the sample tray.

Between the first section 66 and the second section 63 there is preferably a constriction 64 in the compartment walls. This constriction retains the strip in place in the tray 8 and allows fluid to pass into the second section 63. Other means can be used to retain the strip in place.

The second section 63 is a "dam section" which retains solutions during rocking, but passes solutions to the third section 62 during draining. This third section, the "drainage section", may have an open end through which solutions flow to a waste receptacle. The open end can be notched 61 to enhance drainage.

The tray is pivoted about an axis of rotation, with the third section being furthest from the axis of rotation. The tray is gently rocked (e.g., a maximum inclination of about 12 degrees) to enable the reagent, sample or wash solution to spread evenly over the strip means and mix uniformly with any soluble reaction components already in the tray. The tray is deeply tilted (e.g., an inclination of 50 degrees) to drain the solutions away from the strip means.

FIG. 2 illustrates the dam section having a floor that is inclined upwardly when in an operational position. This section prevents a solution from moving into the drainage section during rocking, but allows the fluid to pass to the third section during drainage. In order to retain fluid during rocking, the angle of inclination of the compartment floor must, therefore, be greater than the greatest angle of inclination of the sample tray during rocking. Desirably, the inclination of the floor is about 15 degrees and the maximum angle of rotation during rocking is 12 degrees.

The drainage section preferably has a floor inclined in a downward direction at an angle greater than the greatest angle of rotation during the rocking operation. This section receives and drains fluid. Desirably, the inclination of the floor is about 15 degrees and the maximum angle of rotation during rocking is 12 degrees. The angle of inclination is greater than the greatest angle of rotation of the sample tray during rocking in order to prevent the back flow of waste solutions.

Desirably, the second section is less than half as long and 20 to 50 percent wider than the first section. This ratio permits sample volume to be accommodated without unnecessary sacrifice of compartment length. The third section is also desirably less than half as long as the first section.

The compartments may comprise a central strip section, two immediately adjacent dam sections, and two peripheral drainage sections, or merely one of each type of section, depending on where the axis of rotation lies.

The sample tray is held in a sample tray support 4 that includes a means for holding the tray and means for rocking and draining the tray. One embodiment of the sample tray has notches that receive protrusions in the sample tray support. Alternatively, the sample tray can have the protrusions. The protrusions can be on two opposite sides of the sample tray such that the sample tray slides horizontally into place. The sample tray can also have protrusions on its bottom portion such that the sample tray can be lowered into the sample tray support and held in place by the protrusions.

The sample tray support must allow pivoting about the axis of rotation, thereby allowing rocking and draining of the sample tray. If the axis of rotation is near the center of mass of the sample tray and its support, the force needed to drive rotation is minimized and the space required for rocking and draining is minimized.

The means to permit rocking and draining can be a pivoting connection, such as an axle or hinge. If the axis of rotation is below the sample tray and its holder, the tray and its holder must describe an arc. If the axis of rotation runs through the sample tray holder, but on an end of the tray, one end of the sample tray remains essentially fixed and the other end moves up and down. The sample tray support must be able to engage the driving means for rocking and draining. Any standard coupling means can be used to connect the sample tray support to the step motor.

The rocking and draining mechanism of this invention is desirably provided by a single "step motor." The step motor 19 rotates the tray both clockwise and counterclockwise about an axis of rotation 30. This axis of rotation can be about a shaft of the step motor that is mounted below the tray. Desirably, the axis of rotation falls near the center of mass of the tray and its support. The shaft of the motor alternates in rotation between the clockwise and counterclockwise directions, thereby, rocking the tray and causing a solution in the tray to wash back and forth over the reaction strip. The solution is drained from the tray by rotating the shaft of the step motor to a "maximum angle" of rotation for the tray. This maximum angle of rotation for the tray is significantly greater than the angle of rotation reached by the tray during the rocking operation. The drainage position is held of the tray is desirably held for a time sufficient to drain the tray or for several seconds. A motor drive card determines the sequence of rocking and draining. The sequence can be controlled either on the basis of time elapsed or number of cycles performed.

Figure 3:
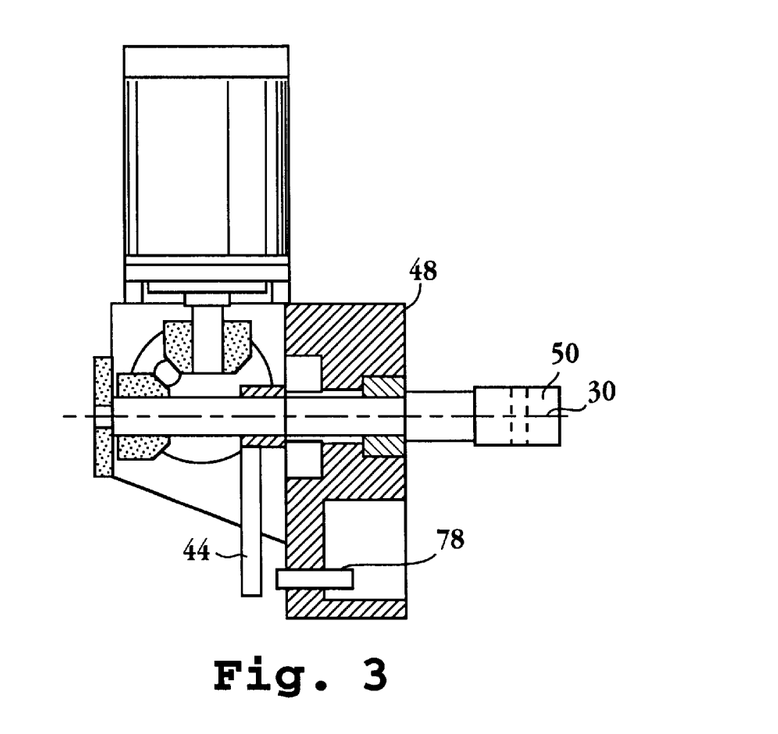
FIG. 3 is a front sectional view of the drive mechanism for rocking and draining the sample tray.

FIG. 3 illustrates a shaft 50 that extends along the axis of rotation and is coupled to the sample tray holder. The shaft is horizontal, and its angle of rotation is the same as the angle of inclination of the sample tray. The shaft is mounted in a housing 48. In the housing are the homing sensor 77, a first contact sensor 78, and a second contact sensor 79. Desirably, the sensors are electromagnetic.

Figure 4:
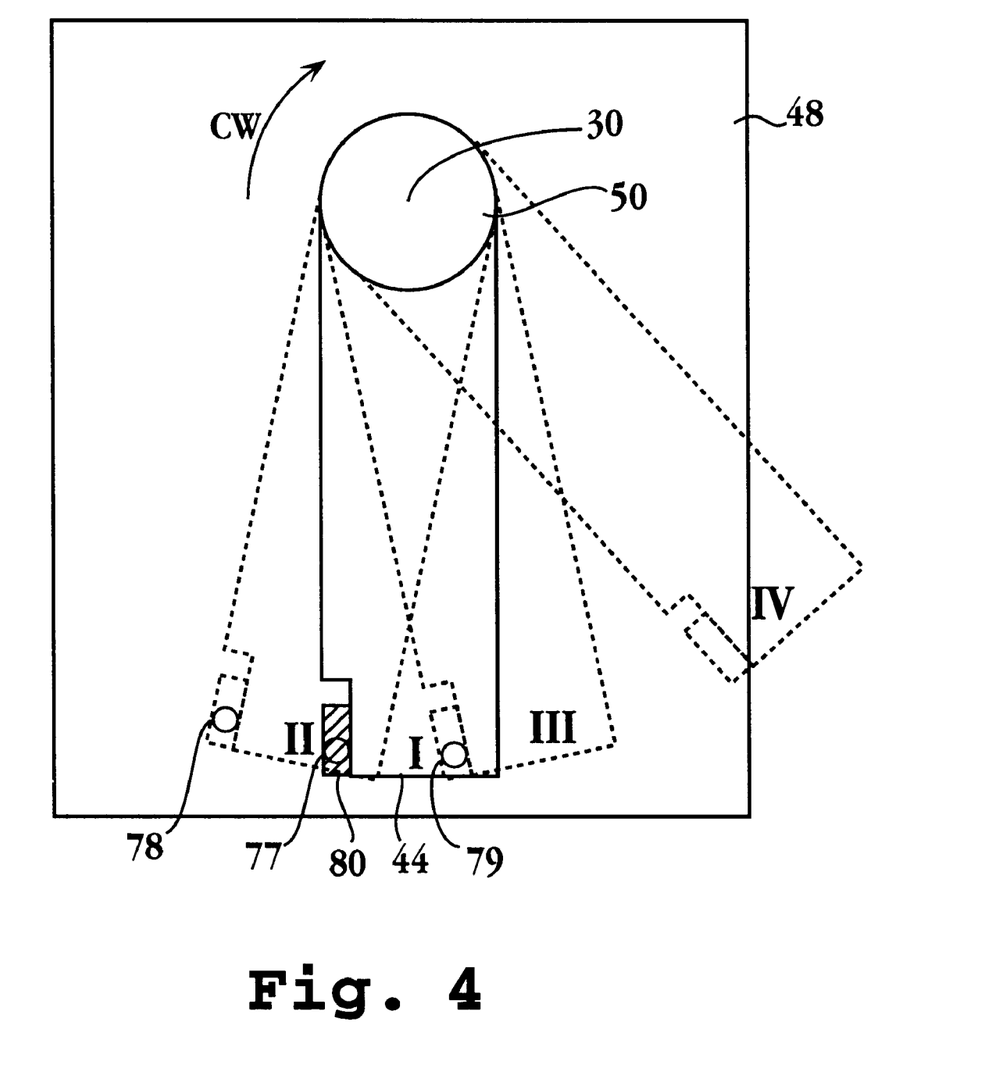
FIG. 4 is a side view of the rocking and draining mechanism.

FIG. 4 illustrates a sensing block 80 that is attached to a perpendicular extension of the shaft 44. The sensing block is attached desirably at the point furthest from the shaft to provide greatest precision in sensing the angle of rotation. As the shaft turns, an arc is ascribed. The sensing block is detected by the homing sensor 77, the first contact sensor 78, and the second contact sensor 79 at predetermined points corresponding to certain angles of rotation.

Figure 5:
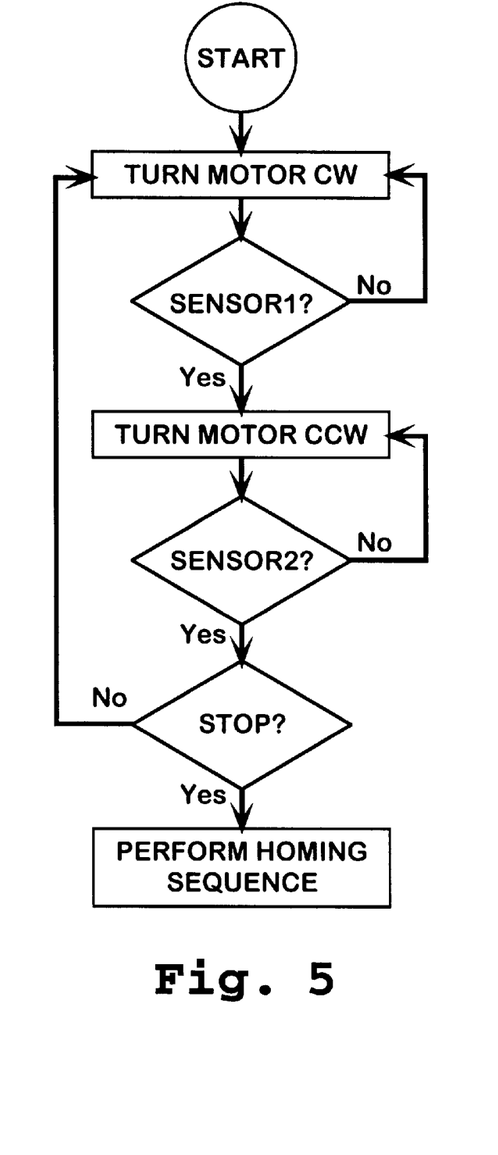
FIG. 5 is a diagram of the sensors and positions.

FIG. 5 illustrates the logic for the rocking cycle that first turns the motor clockwise until the first contact sensor 78 is activated at Position II. The angle of rotation of the shaft and the angle inclination of the tray at this point is desirably 12 degrees from the home position or "Position I." The motor then turns counterclockwise until these second contact sensor 79 is activated at Position III. From this position, one of three operations can be programmed to occur, depending on the control circuitry. The sequence of tray motion can be repeated, directed into the homing sequence, or directed into the drainage cycle.

Figure 6:
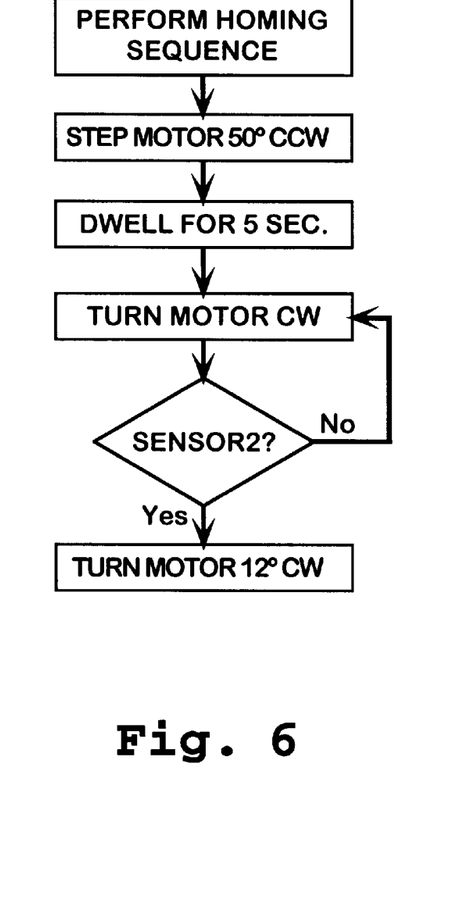
FIG. 6 is a diagram of the control logic for rocking.

FIG. 6 illustrates the homing sequence that begins with either clockwise or counterclockwise rotation of the tray. When either the first contact sensor 78 or the second contact sensor 79 is activated, rotation of the tray by 12 degrees to Position I occurs and the homing sensor is activated.

Figure 7:
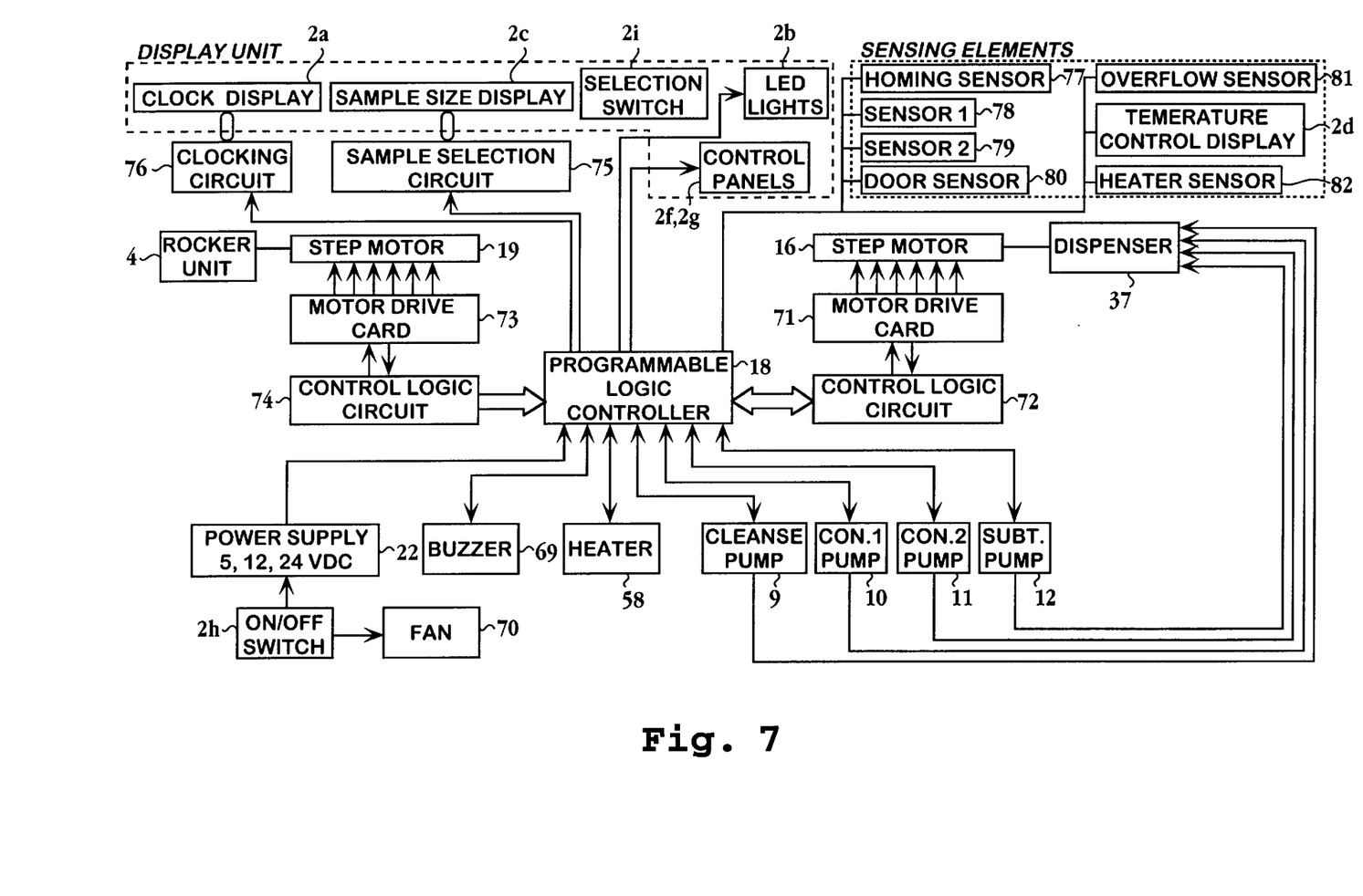
FIG. 7 is a diagram of the control logic for draining.

FIG. 7 illustrates the drainage cycle that begins with the homing sequence. The step motor rotates counterclockwise, desirably by 50 degrees, and remains in that position for desirably 5 seconds. The step motor then rotates clockwise until the second contact sensor 79 is activated and rotation by another 12 degrees in a clockwise direction to Position I occurs. This activates the homing sensor.

Figure 8:
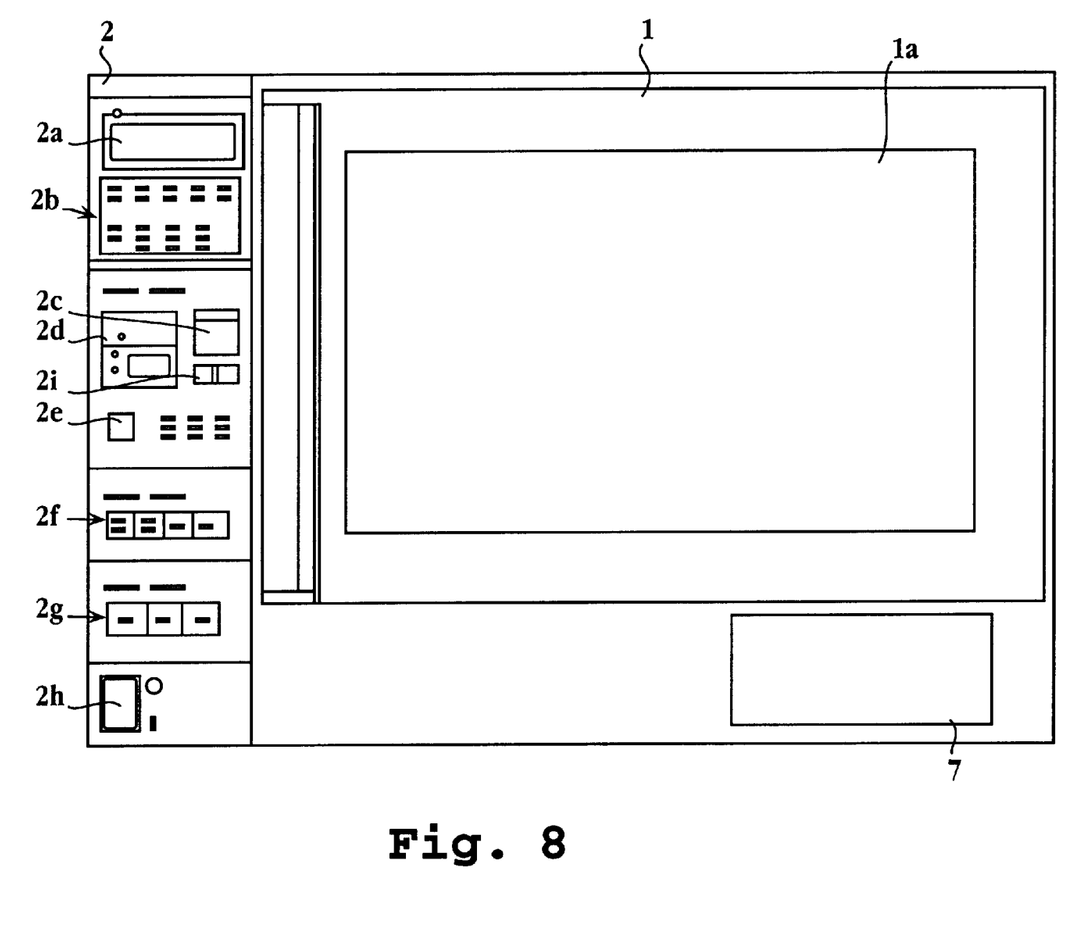
FIG. 8 is a block diagram showing the control components and their relationships.

FIG. 8 is a block diagram illustrating the preferred control components and their relationships. A programmable logic controller 18 can accept multiple inputs and has multiple outputs. The programmable logic controller 18 monitors and controls all functions, either directly or indirectly. Power is supplied through the programmable logic controller 18 to all other components. Where certain functions depend on operator input, the programmable logic controller 18 provides the logic to operate the apparatus. For example, the operator selects the number of samples using the sample selection circuit 75. This selection enters the program to compute the necessary operation, and parameters of the step motor 16 that drives the dispenser 37, as well as the pumps that provide solutions through the dispenser.

Desirable embodiments of the apparatus have control means for performing immuno-assays at different temperatures. These control means allow the apparatus to conduct a "short" assay performed at about 37 degrees Celsius or a "long" assay performed at room temperature. The timing of rocking and draining operations for an assay varies depending upon the mode selected. Motor drive cards, control logic circuits, and a programmable logic controller are desirably used to control the sequence of rocking and draining with this apparatus. These control means also direct the solution-dispensing function of this apparatus.

The programmable logic controller 18 and the selections of the operator desirably direct the apparatus in to one of five modes of operation. The first mode of operation is the "standby" mode. The machine is not ready to perform any operation in this mode and is "powering-up." The second mode of operation is the "idle" mode. The machine is ready for operation and all the indicators are off. The third mode of operation is the "operating" mode. The machine is performing either a LONG or SHORT assay test in this mode. The machine remains in this state until the assay is completed or terminated. The fourth mode of operation is the "halt" mode. The current process in this mode is temporarily halted. The mode of operation reverts to the operating mode when START/HALT button is pressed. The fifth mode of operation is the "fail" mode. The machine is in this mode only if the machine overheats. The machine can be reset from this mode only by terminating the power and allowing the machine to cool down.

Control logic circuit 74 and the motor drive card 73 provide the control logic of FIGS. 5, 6, and 7. The amount of flexibility desired for the operation of the apparatus affects the amount of control that is provided by the control logic circuit and the motor drive card. The operator's selection of the "short mode" at an elevated temperature or a "long mode" at room temperature affects the timing of dispensing, the number of cycles or amount of time spent in the various rocking cycles, the heater, and the functioning of a buzzer or other alarm.

Table 1 shows the operating conditions for the short and long assays of the preferred embodiment of this invention. The long mode of operation requires 16 to 30 hours, desirably 21 hours, at room temperature. The short mode requires 3 to 8 hours, desirably 5 hours, at about 37 degrees C.

TABLE 1

Conditions for Short and Long Assays

| Applied solution | Short assay (37 degC) | Long assay (ambient) |
| --- | --- | --- |
| Serum incubation | 3 hr | 18 hr |
| Washer solution | 3 × 5 min. | 3 × 5 min. |
| Conjugate 1 | 30 min. | 60 min. |
| Washer solution | 3 × 5 min. | 3 × 5 min. |
| Conjugate 2 | 30 min. | 30 min. |
| Washer solution | 3 × 5 min. | 3 × 5 min. |
| Substrate | 15 min. | 15 min. |

The apparatus as illustrated in FIG. 7 has a power supply 22 that desirably provides direct current at a voltage level of 5, 12, or 24 Volts. An on/off switch 2h activates the power supply and automatically powers a fan 70 that cools the power supply.

A buzzer 69 is provided. The buzzer 69 is desirably activated in a short burst when an assay is completed or a sustained tone when the incubation chamber overheats and the operation of the apparatus must be terminated. It can also be programmed for other patterns of sound or to sound for other conditions.

A heater 58 provides temperatures from room temperature to 100 degrees Celsius. The Western Blot Assay is performed at room temperature or at temperatures no higher than about 45 degrees Celsius, desirably no higher than 37 degrees Celsius.

Four separate pumps, 9, 10, 11, and 12, are used to dispense washing buffer, Conjugate 1, Conjugate 2, and Substrate. Desirably, the pumps are close to the sample tray and to the reagent containers to minimize waste.

Reagent and wash solutions are desirably placed in color coded bottles and dispensed by color coded tubing. The volume of solutions dispensed to the sample compartments is desirably at least 1 ml and desirably 2 ml for a tray having a strip section of approximately 10 cm by 1 to 2 cm. The aggregate volume of solutions dispensed depends on the number of samples being assayed. A desirable solution container volume is 500 ml for washing buffer and 150 ml for reagent solutions. The approximate volume of reagent solutions required for a complete assay of a full sample tray is desirably about 500 ml of wash buffer and about 60 ml of each reagent solution.

Each solution has its own tubing and pump and its own port in a movable dispenser 37. The dispenser moves on a track and is positioned such that solutions are dispensed into the strip section of each compartment. To avoid cross-contamination of solutions because of "clinging" drops, the ports on the dispenser desirably extend from the dispenser head on small tubes projecting downward toward the sample tray.

In the preferred embodiment, control of the dispensing is done by a step motor 16 which is driven by a changeable motor drive card 71 and the control logic circuit 72. The control logic circuit interacts with the programmable logic controller. The degree of flexibility desired for the apparatus affects the amount of control that is provided by the control logic circuit and the motor drive card.

The step motor advances the dispenser along a dispensing slide mechanism 13. The step motor connects at the driven end 15 of the slide mechanism and moves the dispenser by means of a cord, chain, or equivalent flexible device wrapped around a drive star and a passive end.

The number of samples for which dispensing occurs is set by the operator in a sample selector 2i. The number of samples is shown on a display 2c and entered in a sample selection circuit 75 that interacts with the programmable logic controller. The number of samples affects the dispensing function, but has no relevance to the rocking and draining functions. The sample size includes a positive and a negative control and at least one sample to be assayed.

There are a variety of options available to accommodate variable sample size with the control logic. The simplest option to perform is to make no change. Solutions can be dispensed as if all compartments had samples. Alternatively, pumps can be programmable operate only for those dispensing positions for which there was a sample but all dispensing positions are visited. Another alternative is where only certain dispensing positions are used. The selection of an embodiment will depends on the relative importance of time, simplicity of control logic, and conservation of reagent solutions.

Time elapsed during the operation of the apparatus is a variable that can be applied to govern many functions of the apparatus including rocking, draining, and dispensing. The time elapsed is shown on a clock display 2a and the clocking circuit 76 provides input to various apparatus functions through the programmable logic controller. The clocking circuit can be based on actual time elapsed since the assay began, or it can approximate the time elapsed based on the progress of the assay according to programmed logic and a counting of events.

Desirably, pressing a START/HALT button begins the assay. A timer records the time lapse of the test assay in an "hours and minutes" format. Dispensing and drainage of fluids is performed automatically at preprogrammed time intervals. After the dispensing of each fluid, its corresponding status light illuminates. On test completion the "END" light illuminates and a buzzer sounds. If another test is to be performed, the END button is pressed to reset the machine. The whole cycle is then repeated.

Desirably, the programmable logic controller allows for temporary interruption of operation. Pressing the START/HALT button during a test run terminates the operation of the machine. The opening of a door while performing a test also halts the machine. The rocker tray halts in the horizontal position, and the heater is deactivated. The process can also be terminated bin the preferred embodiment by pressing an ABORT button.

A variety of sensing elements can be used with the apparatus. The homing sensor 77, the first contact sensor 78, and the second contact sensor 79 are used to control the rocking and draining means. The door sensor 80 actuates if the door is open and halts the operation of the apparatus. The overflow sensor 81 monitors the level of waste in the waste container 7.

The heater sensor 82 measures the temperature in the incubation chamber. Through the programmable logic controller, it activates the buzzer 69, if a preset temperature is exceeded, and halts the assay. The operation of the apparatus must then be terminated until the apparatus cools. The temperature control display 2d shows the temperature.

FIG. 8 is a front view of the automated Western Blot Assay apparatus illustrating the control and monitoring features. The apparatus has a door 1 with a glass (shatter proof) window 1a at the front. Desirably, the sample tray holder slides out through the door when the door is open. The interior is illuminated to allow observation of the test.

Normally, the operator is not required to attend to the machine during its operation. The controls available on the front panel are mainly for mode selection and exceptional circumstances for example, when the door is accidentally opened during an assay. Before using the machine the operator checks to ensure that the drainage trough and removable waste container are in place. Pressing a STANDBY button prepares the machine for a test run.

The front of the apparatus has a display unit 2 which desirably includes a clock display 2a, LED lights 2b indicating process status, sample size display 2c, sample size selection 2i, temperature control display 2d, long mode/short mode selection 2e, process control panel 2f, special function panel 2g, on/off switch 2h, selection button 2i, and a removable waste container 7. The various indicator lights and buttons are color-coded to reduce the risk of error. Desirably, warning lights are red. Green and yellow are desirable colors used to indicate status or function. Desirably, indicator lights and buttons are arranged to further reduce the risk of error, clustering them as to function. A timer shows the time lapse, since start of the assay in hours and minutes. Desirably, the machine buttons and indicators are grouped in four categories.

The four categories of controls are: 1. STATUS/CONTROL A; 2. STATUS/CONTROL B; 3. WARNING INDICATORS; and 4. MANUAL OVERRIDES. The following is a detailed description of each of these controls for the preferred embodiment.

The following six controls or lights are categorized as "STATUS/CONTROL A."

(1) The START/HALT control is green. This button is used for starting, halting (temporary stoppage) and restarting the assay. When the machine is in the idle state, none of the lights in STATUS/CONTROL A and WARNING INDICATORS are illuminated. This button will start the assay and put the machine into the run state. The start of assay is indicated by the OPR light. On pressing this button again, the machine is in the "halt" mode. This is indicated by the PAUSE light. The OPR light remains on as the assay can be restarted by pressing the START/HALT button again.

(2) The OPR light is green. This light indicates that the machine is in the operating state. It is activated by the START/HALT button and remains illuminated until either the assay is completed or terminated.

(3) The CON 1 light is yellow. This is a progress status light. Its activation indicates that conjugate 1 has been applied. The light terminates when the agitation with conjugate 1 is completed, as indicated by the END light. The light also terminates if the process is terminated.

(4) The CON 2 light is yellow. This is a progress status light. Its activation indicates that conjugate 2 has been applied. The light goes off when the agitation with conjugate 2 is completed, as indicated by the END light. The light also terminates if the process if terminated.

(5) The SUBT light is yellow. This is a progress status light. Its activation indicates that substrate has been applied. The light terminates when the agitation with substrate is completed, as indicated by the END light. The light also terminates if the process is terminated.

(6) The END button is red. When the assay is completed, the END light is activated. All the progress status lights and the OPR light terminates. The END light remains illuminated until this button is pressed. Pressing the END button allows the machine to operate in the idle state. The operator can then do another test by pressing the START/HALT button.

The following four controls or lights are categorized as "status/control B".

(1) The MODE SELECTOR button is yellow. It selects between the two available modes, LONG and SHORT. Pressing the button changes the mode. The default mode is the SHORT mode. Mode selection is possible only when the machine is idle. Pressing this button when the machine is running has no effect.

(2) The LONG light is yellow. This indicates that the machine is in the LONG mode. The HEATER ON light does not illuminate during this mode because the LONG mode operates under room temperature.

(3) The SHORT MODE light is yellow. This indicates that the machine is in the SHORT mode. The HEATER ON light is also illuminated while the assay is being performed.

(4) The HEATER ON light is yellow. This light illuminates when the heater is activated. There is no heating under the following conditions: 1. when the machine is idle (OPR light off); 2. when the machine is operating in the LONG mode (LONG MODE light on); 3. when the machine is in the halt state (PAUSE light on); and 4. when the machine overheats (OVERHEAT light on).

The following four lights are warning indicators.

(1) The PAUSE light is red. It indicates that the machine is in the halt state. The machine is in to the halt state when 1) the START/HALT button is pressed while assay is running and 2) the door is accidentally opened. The machine continues from the halt state only by pressing the START/HALT button.

(2) The OVERHEAT light is red. This indicates that the temperature has exceeded its preset value. The machine detects this condition and automatically terminates the assay. The machine cannot be restarted by pressing the START/HALT button. The only option is to turn the power off.

(3) The STANDBY light/button is red. This light indicates that the machine is in the standby state or the "default" state when the power is on. It is incorporated as a safety feature to alert the users to do the necessary start up procedure before switching the machine to the idle state. Pressing this button brings the WBA to the idle state and turns this light off.

The following three buttons are manual overrides. These buttons have covers to prevent accidental usage.

(1) The ABORT button is red. This button is used to terminate the assay. This is different from the halt state in that the terminated assay cannot be restarted with the START/HALT button.

(2) The OVERRIDE button/light is red. When the assay is terminated unexpectedly, there can be some fluid left in the sample tray. This button allows the user to drain the tray. The light indicates that the drainage is in process.

(3) The FLUSH button/light is red. This enables user to flush the reagents from the pumps. This button is also used in the start-up procedures for the initial pumping of reagents. The button is a self-latch type, with light indication, i.e., the reagents are continuously pumped from the bottles as long as the switch is in the "on" position. When the light is on, all pumps activated together.

Two tones are made by the preferred embodiment of this machine. These tones include the assay completion tone. This tone is a short tone alerting the user that the assay is completed. The overheat tone is a continuous tone alerting the user that the machine temperature has exceeded its preset value. When the machine overheats, the power must be terminated and the oven temperature checked. If the oven temperature is correct, then the cut-off temperature must be reset using the controls located under the side cover.

There are several desirable features in the fluid dispensing mechanisms of the preferred embodiment of this invention. The tubing from the conjugate and substrate bottles connects directly to the dispensers in the machine. To prevent cross-contamination, bottles must be placed correctly. The following color-code scheme facilitates this: Conjugate 1 is White; Conjugate 2 is Blue; and the Substrate is Grey. These color markings are on both the bottles and the chemical tray. The washer solution is contained in the largest bottle.

Each dispensing operation dispenses 2 ml of solution to each of the 27 slots on the sample tray. The minimum volume for each test run is, therefore, 54 ml for each of the conjugates, and the substrate, and 486 ml for the washer buffer. An additional 5 ml or more of each reagent is recommended in every test so as to avoid bubbles when the bottles are almost empty.

The pumps are to be pre-filled with reagents so that accurate dosage can be ensured. To perform the pre-pumping step, the chemical bottles must be properly connected. A container must be placed under the nozzles, and then the "Flush" button must be pressed. All the pumps are activated together. Sufficient time should be allowed for the pumps to pump reagents through the lengths of the tubing. After the first drops of chemicals appear at the nozzles, the "Flush" button should be pressed again. The indicating light in the button will turn off and the pumping cease. The pumps are ready for the assay.

I claim:

1. A tray for conducting assays which comprises a plurality of substantially parallel adjacent elongated compartments, each of said compartments being defined by a bottom and a pair of side walls extending the length thereof, and an end wall connecting said walls at one end thereof, the end opposite said end wall being open, each said compartment being divided into a first section for receiving a solution, a second section having a floor inclined upwardly in the direction of said open end for retaining the solution when the tray is rocked, and a third drainage section that receives and drains the solution when the tray is tilted further so that the solution escapes the second section, the third drainage section having a floor inclined downwardly in the direction of said open end through which the solution flows into a receptacle, wherein the first, second and third sections of a compartment are in fluid communication upon tilting.

2. The tray of claim 1, wherein the third section has a downwardly inclined floor so as to hinder backflow.

3. The tray of claim 2, wherein the first and second sections are divided by a constriction which permits liquids to pass between the sections but acts to retain a solid object larger than the constriction in said first section.

4. A tray for conducting assays which comprises a plurality of substantially parallel adjacent elongated compartments, each of said compartments being defined by a bottom and a pair of side walls extending the length thereof, and an end wall connecting said walls at one end thereof, the end opposite said end wall being open, each said compartment being divided into a first section for receiving a solution, said first section having a reactant strip means retained therein, a second section having a floor inclined upwardly in the direction of said open end for retaining the solution when the tray is rocked, and a third drainage section that receives and drains the solution when the tray is tilted further so that the solution escapes the second section, the third drainage section having a floor inclined downwardly in the direction of said open end through which the solution flows into a receptacle, wherein said first, second and third sections of a compartment are in fluid communication, and said first sections of said compartments are not in fluid communication.

5. The tray of claim 4, wherein the third section has a downwardly inclined floor so as to hinder backflow.

6. The tray of claim 5, wherein the first and second sections are divided by a constriction which permits liquids to pass between the sections but acts to retain the reactant strip means in said first section.

7. A tray for conducting assays which contains a single compartment said compartment being defined by a bottom and a pair of side walls extending the length thereof and an end wall connecting said walls at one end thereof, the end opposite said end wall being open, each; said compartment being divided into a first section for receiving a solution, a second section having a floor inclined upwardly in the direction of said open end for retaining the solution when the tray is rocked, and a third drainage section that receives and drains the solution when the tray is tilted further so that the solution escapes the second section, wherein the third drainage section has a floor inclined downwardly in the direction of said open end, and the first, second and third sections of a compartment are in fluid communication upon tilting.

* * * * *